US010206727B2

(12) United States Patent
Ponce et al.

(10) Patent No.: US 10,206,727 B2
(45) Date of Patent: Feb. 19, 2019

(54) APPARATUS FOR THE FIXATION OF PROXIMAL HUMERUS FRACTURES

(71) Applicant: Wright Medical Technology, Inc., Memphis, TN (US)

(72) Inventors: Brent A. Ponce, Homewood, AL (US); John Whitcomb, Birmingham, AL (US)

(73) Assignee: Wright Medical Technology, Inc., Memphis, TN (US)

( * ) Notice: Subject to any disclaimer, the term of this patent is extended or adjusted under 35 U.S.C. 154(b) by 446 days.

(21) Appl. No.: 14/760,316

(22) PCT Filed: Jan. 10, 2014

(86) PCT No.: PCT/US2014/011113
§ 371 (c)(1),
(2) Date: Jul. 10, 2015

(87) PCT Pub. No.: WO2014/110421
PCT Pub. Date: Jul. 17, 2014

(65) Prior Publication Data
US 2015/0359576 A1     Dec. 17, 2015

Related U.S. Application Data

(60) Provisional application No. 61/751,485, filed on Jan. 11, 2013.

(51) Int. Cl.
*A61B 17/80* (2006.01)
*A61B 17/17* (2006.01)
*A61B 17/88* (2006.01)

(52) U.S. Cl.
CPC ...... *A61B 17/8061* (2013.01); *A61B 17/1739* (2013.01); *A61B 17/809* (2013.01);
(Continued)

(58) Field of Classification Search
CPC ... A61B 17/1728; A61B 17/80; A61B 17/808; A61B 17/8061; A61B 17/1739
See application file for complete search history.

(56) References Cited

U.S. PATENT DOCUMENTS 7,655,029 B2 *  2/2010  Niederberger ..... A61B 17/8061
                                              606/280
7,896,886 B2 *  3/2011  Orbay ................ A61B 17/1717
                                              606/62
(Continued)

FOREIGN PATENT DOCUMENTS

CN       201920886 U      8/2011
CN       102835998 A     12/2012
(Continued)

OTHER PUBLICATIONS

Examination report No. 1 issued in connection with Australian patent application No. 2017203925, dated Dec. 4, 2017, 4 pages.
(Continued)

*Primary Examiner* — Anu Ramana
(74) *Attorney, Agent, or Firm* — Duane Morris LLP

(57) ABSTRACT

In some embodiments, apparatus for the fixation of proximal humerus fractures includes an implantable humerus plate having a proximal portion adapted to be positioned at a head and medial calcar of the humerus, a distal portion adapted to be positioned along a shaft of the humerus, and a plurality of calcar openings provided through the proximal portion adapted to receive calcar fasteners that extend into the medial calcar.

7 Claims, 6 Drawing Sheets

(52) U.S. Cl.
CPC ...... *A61B 17/8019* (2013.01); *A61B 17/8042* (2013.01); *A61B 17/8866* (2013.01); *A61B 17/1778* (2016.11)

(56) References Cited

U.S. PATENT DOCUMENTS

| | | | | |
|---|---|---|---|---|
| 7,927,333 | B2* | 4/2011 | Gradl | A61B 17/746 606/280 |
| 8,142,432 | B2* | 3/2012 | Matityahu | A61B 17/1728 606/54 |
| 8,231,662 | B2* | 7/2012 | Huebner | A61B 17/8033 606/280 |
| 8,968,371 | B2* | 3/2015 | Humphrey | A61B 17/1728 606/282 |
| 9,089,375 | B2* | 7/2015 | Smith | A61B 17/1725 |
| 2004/0225291 | A1 | 11/2004 | Schwammberger et al. | |
| 2005/0165395 | A1 | 7/2005 | Orbay et al. | |
| 2006/0264956 | A1 | 11/2006 | Orbay et al. | |
| 2009/0069851 | A1 | 3/2009 | Gillard et al. | |
| 2010/0076436 | A1 | 3/2010 | Hajianpour | |
| 2010/0324602 | A1 | 12/2010 | Huebner et al. | |
| 2011/0224736 | A1 | 9/2011 | Humphreys | |
| 2012/0179208 | A1 | 7/2012 | Geissler et al. | |
| 2013/0096629 | A1 | 4/2013 | Rollinghoff et al. | |
| 2014/0128921 | A1 | 5/2014 | Parsons et al. | |

FOREIGN PATENT DOCUMENTS

| | | |
|---|---|---|
| EP | 2474278 A2 | 7/2012 |
| WO | 2012/058448 A2 | 5/2012 |

OTHER PUBLICATIONS

Office Action issued in connection with Canadian patent application No. 2,897,974, dated Dec. 19, 2017, 4 pages.

Third Office Action issued in connection with Chinese patent application No. 201480005139.3, dated Jan. 3, 2018, 8 pages.

Second Office Action issued for Chinese patent application No. 201480005139.3, dated Jun. 20, 2017, 17 pages.

International Search Report and Written Opinion issued for corresponding International patent application No. PCT/US2014/011113, dated Apr. 7, 2014, 17 pages.

Patent Examination Report No. 1 issued for corresponding Australian patent application No. 2014205267, dated Feb. 23, 2016, 3 pages.

First Office Action issued for corresponding Chinese patent application No. 201480005139.3, dated Oct. 24, 2016, 16 pages.

Patent Examination Report No. 2 issued for corresponding Australian patent application No. 2014205267, dated Feb. 15, 2017, 6 pages.

\* cited by examiner

APPARATUS FOR THE FIXATION OF PROXIMAL HUMERUS FRACTURES

CROSS-REFERENCE TO RELATED APPLICATION(S)

This application claims priority to U.S. Provisional Application Ser. No. 61/751,485, filed Jan. 11, 2013, which is hereby incorporated by reference herein in its entirety.

BACKGROUND

When a proximal humerus fracture occurs, it is sometimes necessary to fix the bone fragments together to ensure proper healing and restore correct function of the arm and shoulder. Such fixation can be achieved by securing a plate to the lateral side of the humerus adjacent the head of the humerus using screws or pins.

While such procedures can be effective, it is not uncommon for varus collapse to occur in which the head of the humerus collapses and forms an undesirably acute angle (e.g., 80 to 90°) with the neck of the humerus. It is important to prevent such collapse because it can alter the biomechanics of the shoulder joint, decrease range of motion, and lead to unsuccessful outcomes.

In view of the above discussion, it can be appreciated that it would be desirable to have apparatus that enables fixation of proximal humerus fractures but prevents varus collapse.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have apparatus that enables fixation of proximal humerus fractures but that prevents varus collapse. In order to achieve such a result, it is critical to support the medial calcar of the humerus. The calcar is located at the inferomedial portion of the anatomic neck of the humerus. Disclosed herein is apparatus that can be used to restore and support the medial calcar. In some embodiments, the apparatus includes a humerus plate that is provided with a plurality of openings in a calcar region of the plate that enables fasteners to be placed within the inferomedial neck of the humerus. For example, a plurality of small screws can be used to stabilize that region of the humerus to prevent varus collapse. In some embodiments, further fasteners can be threaded directly into the head of the humerus from the medial side of the bone to provide further reinforcement. In such embodiments, an aiming apparatus that attaches to the humerus plate can be used to control the trajectory of the medial fasteners, and potentially the fasteners that extend through the humerus plate as well.

In the following disclosure, various specific embodiments are described. It is to be understood that those embodiments are example implementations of the disclosed inventions and that alternative embodiments are possible. All such embodiments are intended to fall within the scope of this disclosure.

Figures 1, 2:
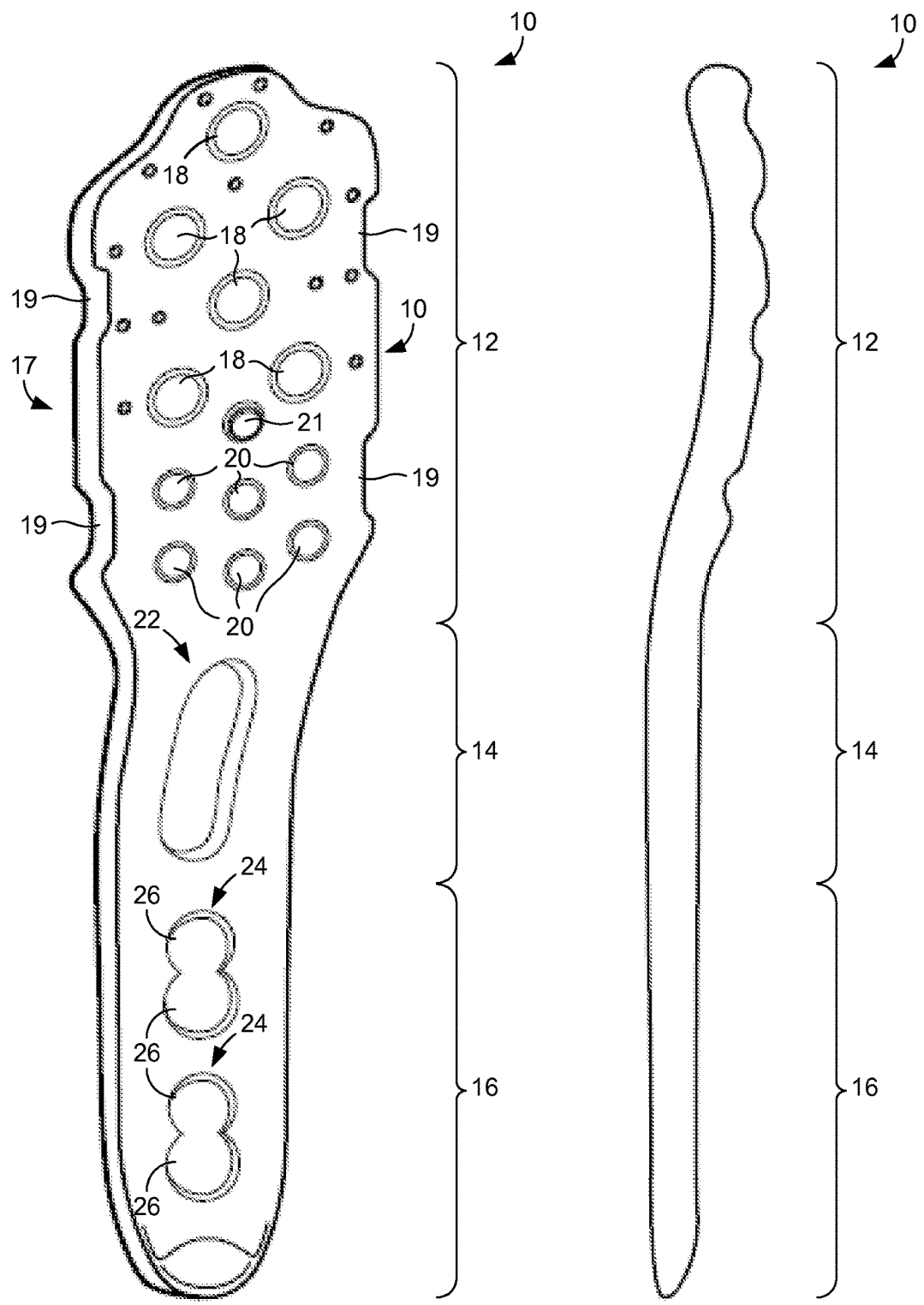
FIG. 1 is a perspective view of a first embodiment of a humerus plate that can be used to fix a proximal humerus fracture.
FIG. 2 is a side view of the humerus plate of FIG. 1.

FIGS. 1 and 2 illustrate an embodiment of an implantable humerus plate 10 that can be used to secure bone fragments of the proximal humerus together. As shown in the figures, the illustrated humerus plate 10 is unitarily formed from a single piece of material, such as stainless steel or titanium. The humerus plate 10 is generally flat, narrow, and elongated so as to be well suited for attachment to the lateral portion of the head, neck, and shaft of the humerus bone. As is illustrated most clearly in FIG. 2, however, the proximal portion 12 of the humerus plate 10 has a gentle curvature that is adapted to match the convex curvature of the head of the humerus bone (see FIG. 4). As is further shown in FIG. 2, however, the central portion 14 and the distal portion 16 of the humerus plate 10 can be generally linear (when viewed from the side). In some embodiments, the humerus plate 10 is approximately 80 to 100 mm long and approximately 2 to 5 mm thick.

With particular reference to FIG. 1, the proximal portion 12 of the humerus plate 10 is wider than the central and distal portions 14, 16 of the plate. In some embodiments, the proximal portion 12 is approximately 18 to 20 mm wide and the central and distal portions 14, 16 are approximately 10 to 14 mm wide. As is further shown in FIG. 1, the proximal portion 12 can have a generally rectangular shape that is defined in part by generally linear lateral edges 17. In some embodiments, the lateral edges 17 include notches 19 that, as described below, facilitate attachment of another device to the humerus plate 10 during the fixation procedure.

With further reference to FIG. 1, each of the portions 12-16 of the humerus plate 10 comprises its own opening or openings. Beginning with the proximal portion 12, there are multiple relatively large openings 18 provided in the upper part of the proximal portion and multiple relatively small openings 20 provided in the lower part of the proximal portion. In some embodiments, the relatively large openings 18 are approximately 3 to 5 mm in diameter and the relatively small openings 20 are approximately 2 to 3 mm in diameter. In the illustrated example, there are six relatively large openings 18 that are generally equidistantly spaced from each other and six relatively small openings 20 that are arranged to two generally parallel rows of three openings each. Notably, greater or fewer numbers of openings and different positioning of the openings can be used depending upon the nature of the fixation that is to be performed. As described below, the relatively large openings 18 are adapted to receive fasteners that will extend into the proximal head of the humerus bone and the relatively small openings 20 are adapted to receive fasteners that will extend into the medial calcar of the humerus bone. In view of this, the relatively large openings 18 may be referred to as proximal openings and the relatively small openings 20 may be referred to as calcar openings. In addition, the calcar openings can be considered as being located in a calcar region of the humerus plate, which is located at a position approximately one-fourth to one-third of the length of the humerus plate, as measured from its proximal end.

In addition to the proximal openings 18 and the calcar openings 20, the proximal portion 12 of the humerus plate 10 can further include at least one drill guide opening 21 that, as described below, can be used to secure another device, such as a drill guide, to the plate during the fixation procedure.

In the illustrated example, the central portion 14 includes a single elongated opening 22 and the distal portion 16 includes two openings 24. In some embodiments, the elongated opening 22 is approximately 3 to 6 mm wide and approximately 12 to 20 mm long. As indicated in FIG. 1, the openings 24 can each comprise dual openings 26 that are joined together at their edges and that enable two independent fasteners to pass. In some embodiments, the openings 26 are each approximately 3 to 6 mm in diameter.

Figure 3:
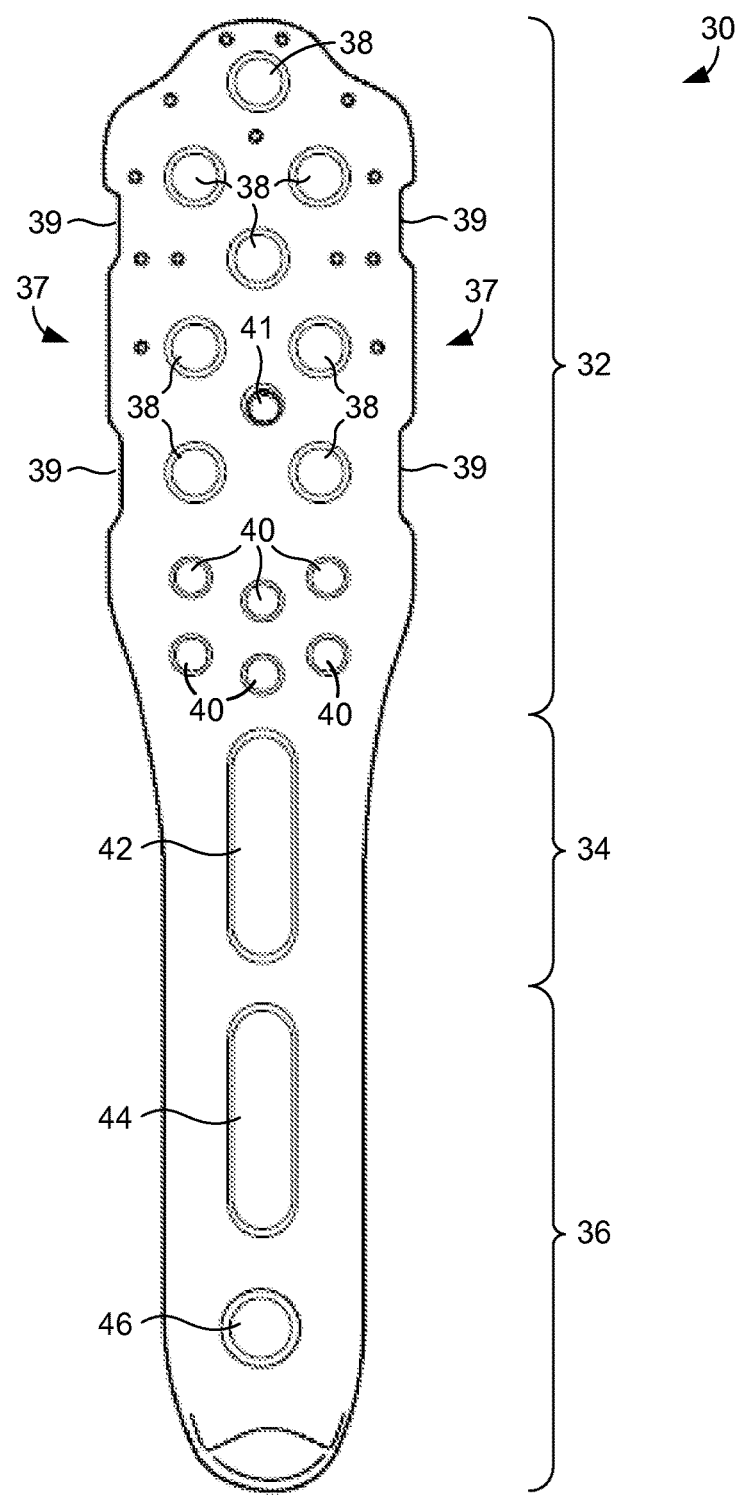
FIG. 3 is a top view of a second embodiment of a humerus plate that can be used to fix a proximal humerus fracture.

FIG. 3 illustrates a second embodiment of an implantable humerus plate 30 that can be used to secure bone fragments of the proximal humerus together. As is apparent from this figure, the humerus plate 30 is very similar to the humerus plate 10 shown in FIG. 1. Accordingly, the humerus plate 30 can be unitarily formed from a single piece of generally flat material and can generally comprise a proximal portion 32, a central portion 34, and a distal portion 36. The proximal portion 32 can have a gentle curvature that is adapted to match the curvature of the head of the humerus bone. As with the humerus plate 10, the humerus plate 30 can be approximately 80 to 100 mm long and approximately 2 to 5 mm thick.

The proximal portion 32 of the humerus plate 30 is wider than the central and distal portions 34, 36 of the plate. In some embodiments, the proximal portion 32 is approximately 18 to 20 mm wide and the central and distal portions 34, 36 are approximately 10 to 14 mm wide. As is further shown in FIG. 3, the proximal portion 32 can have a generally rectangular shape that is defined in part by generally linear lateral edges 37. In some embodiments, the lateral edges 37 include notches 39 that, as described below, facilitate attachment of another device to the humerus plate 30 during the fixation procedure.

With further reference to FIG. 3, each of the portions 32-36 of the humerus plate 30 comprises its own opening or openings. As before, the proximal portion 32 can comprise relatively large proximal openings 38 (~3 to 5 mm in diameter) and relatively small calcar openings 40 (~2 to 3 mm in diameter). As in the previous embodiment, there are eight relatively large openings 38 that are generally equidistantly spaced from each other and six relatively small openings 40 that are arranged to two generally parallel rows of three openings each, although greater or fewer numbers of openings and different positioning of the openings can be used. In addition to the proximal openings 38 and the calcar openings 40, the proximal portion 32 of the humerus plate 30 can further include at least one drill guide opening 41 that can be used to secure another device to the plate during the fixation procedure.

Like the central portion 14 of the humerus plate 10, the central portion 34 includes a single elongated opening 42. However, the distal portion 36 of the humerus plate 30 includes an elongated opening 44 and a circular opening 46. In some embodiments, the elongated openings 42, 44 are approximately 3 to 6 mm wide and approximately 12 to 20 mm long and the circular opening 46 is approximately 3 to 6 mm in diameter.

Figure 4:
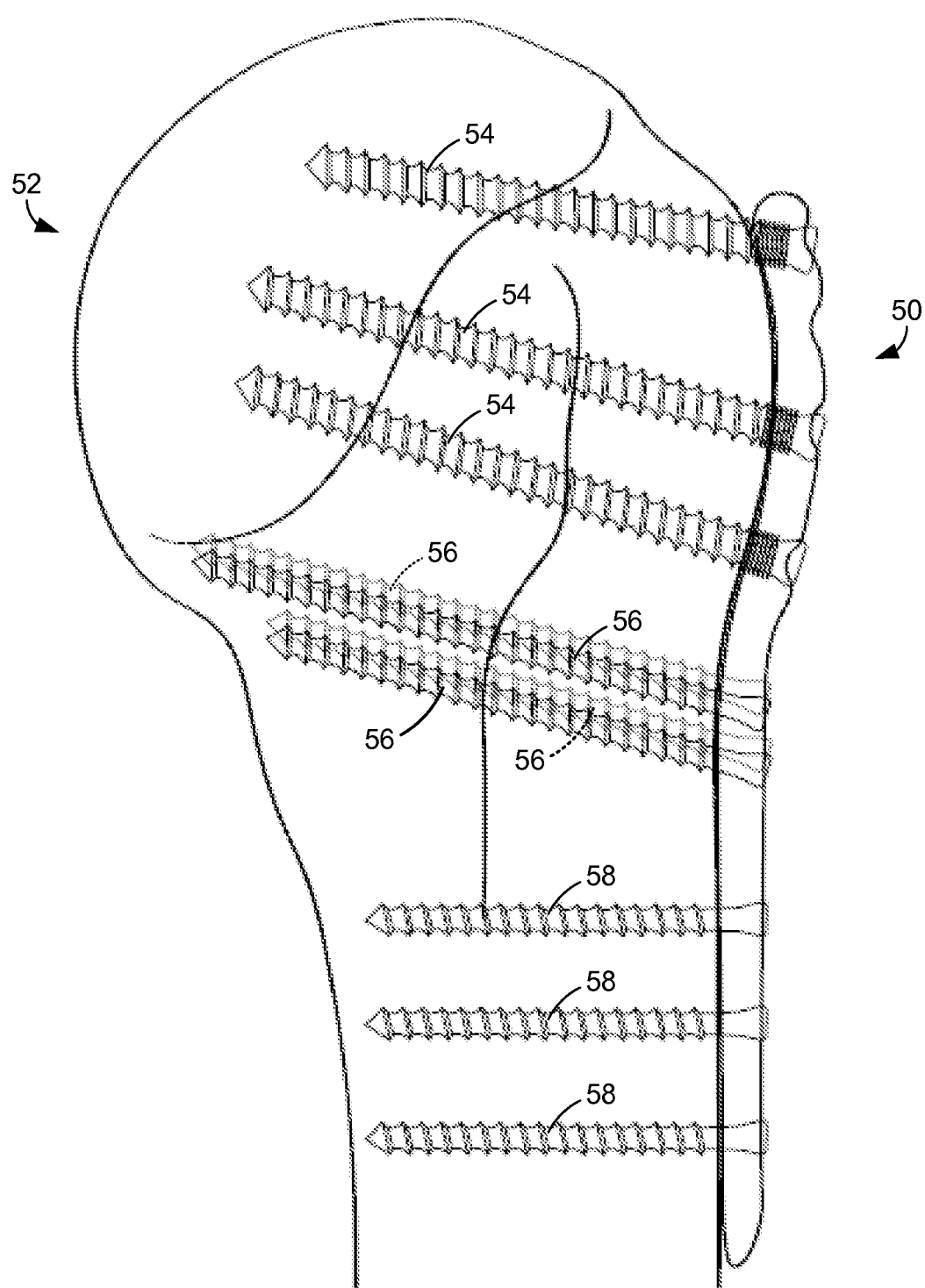
FIG. 4 is a side view of a humerus bone after a humerus plate has been affixed to the bone using bone screws.

Humerus plates of the type described above can be attached to the humeral head, neck, and shaft to fix the bone fragments together and ensure proper healing. In particular, the humerus plate can be applied to the lateral side of the humerus bone and fasteners can be passed through the openings in the plate and into the bone to secure the plate in place, so as to stabilize the bone fragments. In some embodiments, the humerus plate can be secured using bone screws. FIG. 4 illustrates such a scenario. In this figure, a humerus plate 50 having a similar construction to those described above is shown attached to the lateral side of the head, neck, and shaft of a humerus bone 52 with multiple screws. In particular, relatively large proximal screws 54 have been passed through the proximal openings and into the humeral head, relatively small calcar screws 56 have been passed through the calcar openings and into the medial calcar of the humerus, and relatively large central and distal screws 58 have been passed through the central and distal openings and into the shaft of the humerus. Because of the multiple calcar screws 56 inserted into the medial calcar, greater structural integrity is provided to the calcar and the likelihood of varus collapse is greatly reduced.

As indicated in FIG. 4, the proximal screws 54 and the calcar screws 56 can be inserted into the humerus 52 at an angle. In some embodiments, the proximal screws 54 form an angle of approximately 90 to 135° with the horizontal direction (when the patient is in an upright orientation) and the calcar screws 54 form an angle of approximately 90 to 135° with the horizontal direction (again when the patient is in an upright orientation). In some embodiments, the openings of the humerus plate 50 are configured so that the screws 54-58 can only pass through the plate at a predetermined angle. The screws 54-58 can either be solid screws or cannulated screws that have an internal passage that enables them to be passed over a guide, such as a metal pin. In some embodiments, the proximal, central, and distal screws 54, 58 each have a diameter of approximately 3 to 5 mm and the calcar screws 56 each have a diameter of approximately 2 to 3 mm. It is noted that, while bone screws are illustrated in FIG. 4, other fasteners, such as pegs or pins, may be used instead.

Figure 5:
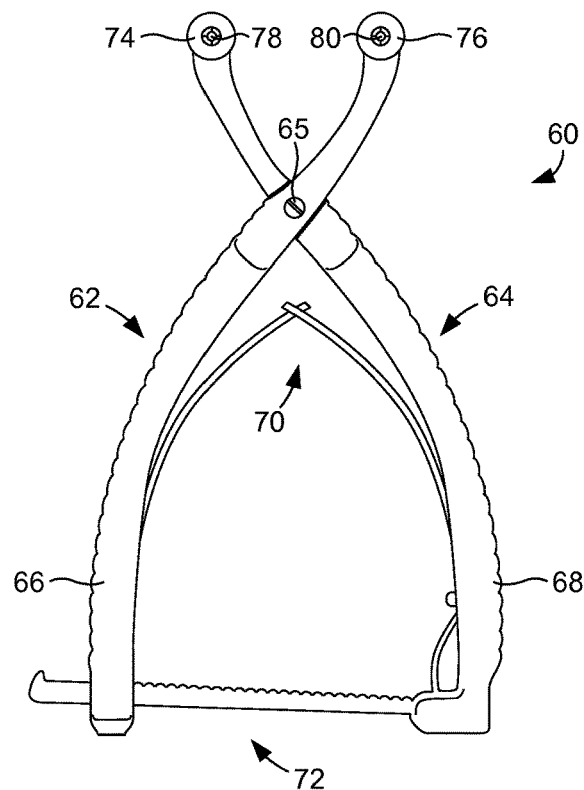
FIG. 5 is a top view of a compression device that can be used in a proximal humerus fixation procedure.
Figure 6:
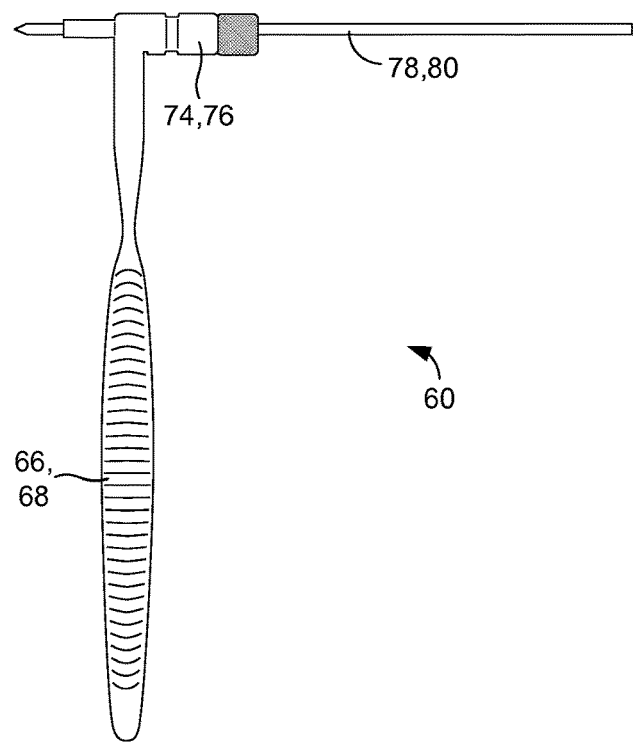
FIG. 6 is a side view of the compression device of FIG. 5.

In some embodiments, fixation of the bone fragments can be achieved by compressing the bone fragments together before inserting all of the fasteners. FIGS. 5 and 6 illustrate an example apparatus suited for this purpose. More particularly, these figures show a compression device 60 that can be used to press the bone fragments together. As indicated FIG. 5, the compression device 60 includes two members 62 and 64 that are connected to each other at a central location along their lengths to form a hinge 65. The proximal portions of the members 62, 64 form grip handles 66, 68 that can be squeezed together by a surgeon or other user. The device 60 includes a spring element 70 that provides resistance to such squeezing and a locking ratchet mechanism 72 that locks the position of the handles 66, 68 when they are released. As the handles 66, 68 are squeezed together, the distance between distal ends 74 and 76 of the members 62, 64 is decreased. As indicated in FIGS. 5 and 6, pins 78 and 80 extend through the distal ends 74, 76 of the members 62, 64. These pins 78, 80 can be driven into the humerus bone using an appropriate driving device, such as a wire driver.

During a fixation procedure, the humerus plate can be attached to the humerus bone using one or more fasteners.

In some embodiments, the fastener or fasteners can be inserted through the humerus plate and into the bone using a drill guide (not shown) that attaches to the humerus plate. By way of example, the humerus plate can be attached to the shaft of the bone using one or more distal screws. Next, the compression device 60 can be positioned relative to the humerus plate so that one of the pins 78, 80 aligns with one of the openings of the plate (e.g., a calcar opening) and one fragment of the bone and the other of the pins aligns with another fragment of the bone that is exposed to the side of the plate. The pins 78, 80 can then be driven into the bone (one passing through the plate and one not). At this point, the grip handles 66, 68 can be squeezed to press the bone fragments together and then the remainder of the fasteners can be passed through the humerus plate and into the bone to secure the fragments while they are in the pressed together state. In this manner, the humerus plate can be affixed while the bone fragments are in an optimal relative position for healing purposes.

In some embodiments, further fasteners can be inserted directly into the head of the humerus to provide additional reinforcement. More particularly, medial fasteners that extend in an anterior-to-posterior direction can be inserted into the humeral head that are perpendicular to the lateral fasteners that pass through the humerus plate. In such cases, an aiming apparatus can be utilized to ensure that the medial fasteners do not intersect the lateral fasteners.

Figure 7:
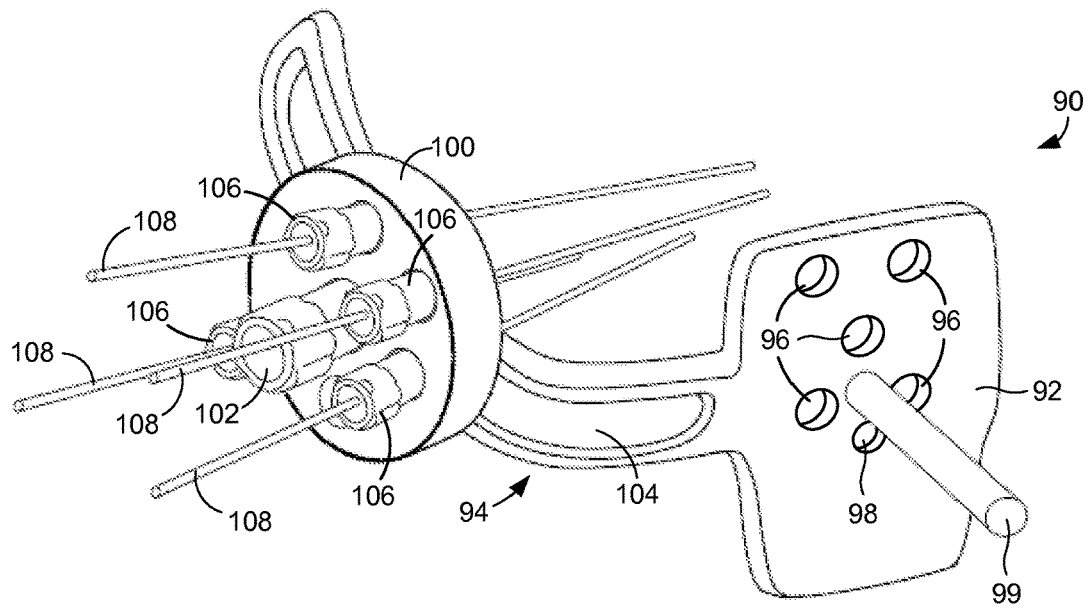
FIG. 7 is a perspective view of an embodiment of an aiming apparatus that can be used in a proximal humerus fixation procedure.

FIG. 7 shows an embodiment of an aiming apparatus 90 that can be used for the above-described purpose. As shown in this figure, the aiming apparatus 90 generally comprises a body 92 that is adapted to attach to the proximal portion of a humerus plate and an elongated arm 94 that extends laterally from the body and that curves to extend in a direction that is generally perpendicular to the plane in which the body resides. As shown in FIG. 7, the body 92 is configured as a generally flat rectangular plate that includes openings 96 that are adapted to align with the proximal openings of the proximal portion of the humerus plate. With such a configuration, the aiming apparatus 90 can be used as a guide for the fasteners that are to be passed through the proximal portion of the humerus plate and into the humeral head. In some embodiments, the body 92 further comprises tabs (not visible in FIG. 7) that are adapted to be received by the notches of the proximal portion of the humerus plate (see FIG. 1 or FIG. 3) so that the body 92 can snap-fit onto the proximal portion of the humerus plate (see FIG. 8). In addition, the body 92 can include a further opening 98 that is adapted to align with a drill guide opening provided in the proximal portion of the humerus plate to facilitate secure fastening of the aiming apparatus 90 to the humerus plate. Furthermore, the body 92 can include a handle 99 that can be used to grip and manipulate the body.

With further reference to FIG. 7, the aiming apparatus 90 also comprises a guide member 100 that is mounted to the arm 94. The guide member 100 secures to the arm 94 with a central fastener 102 that passes through an elongated slot 104 provided in the arm. When the fastener 102 is loose, the guide member 100 can be moved along the length of the arm 94. When the fastener 102 is tightened, however, the position of the guide member 100 along the arm 94 is fixed. With such a configuration, the guide member 100 can be moved along the length of the arm 94 either toward or away from the body 92 and, once the desired position has been reached, the fastener 102 can be tightened to fix the position of the guide member along the arm.

The guide member 100 further comprises multiple guide elements 106 through which pins 108 can be passed. The orientations guide elements 106 are adjustable such that the orientations of the elements relative to the guide member 100 can be changed and fixed in desired orientations. Such adjustability enables the user to control the trajectory of each of the pins 108 so that the pins can be pressed into the head of the humerus with a desired trajectory (i.e., one in which they do not intersect the screws that extend through the humerus plate).

Figure 8:
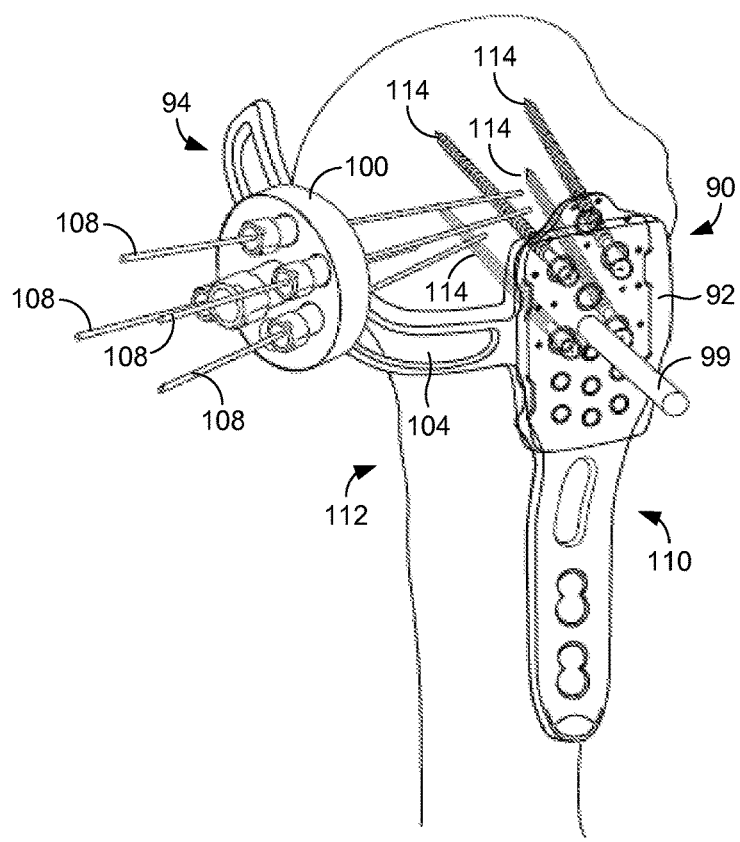
FIG. 8 is a perspective view of a humerus bone during an example proximal humerus fixation procedure.

FIG. 8 shows the aiming apparatus 90 attached to a humerus plate 110, which has been secured to a humerus bone 112 with multiple proximal screws 114. In such a situation, the aiming apparatus 90 can be used to ensure that the medial fasteners (e.g., screws) that will extend in an anterior-to-posterior direction within the humerus head will not intersect the proximal screws 114. To this end, the pins 108 can be passed through the guide elements 106 of the guide member 110 and into the bone 112. If one or more of the pins 108 intersects one or more of the screws 114, as determined by feel or fluoroscopic imaging, the pins can be removed, their trajectories can be changed, and they can be reinserted to see if they clear the screws. Once the pins 108 have been positioned within the bone 112 to the satisfaction of the surgeon, fasteners, such as cannulated screws, can be passed over the pins and the pins can be removed.

Figure 9:
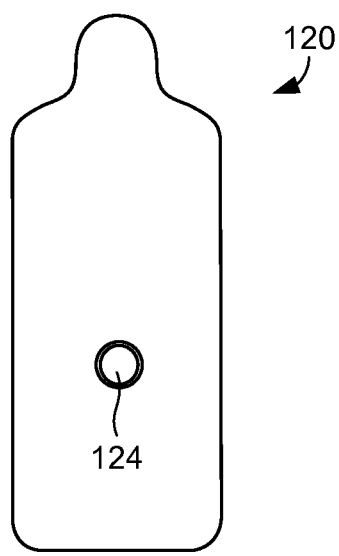
FIG. 9 is a top view of a locking plate that can be used to prevent loosening of fasteners used to secure a humerus plate to a humerus bone.
Figure 10:
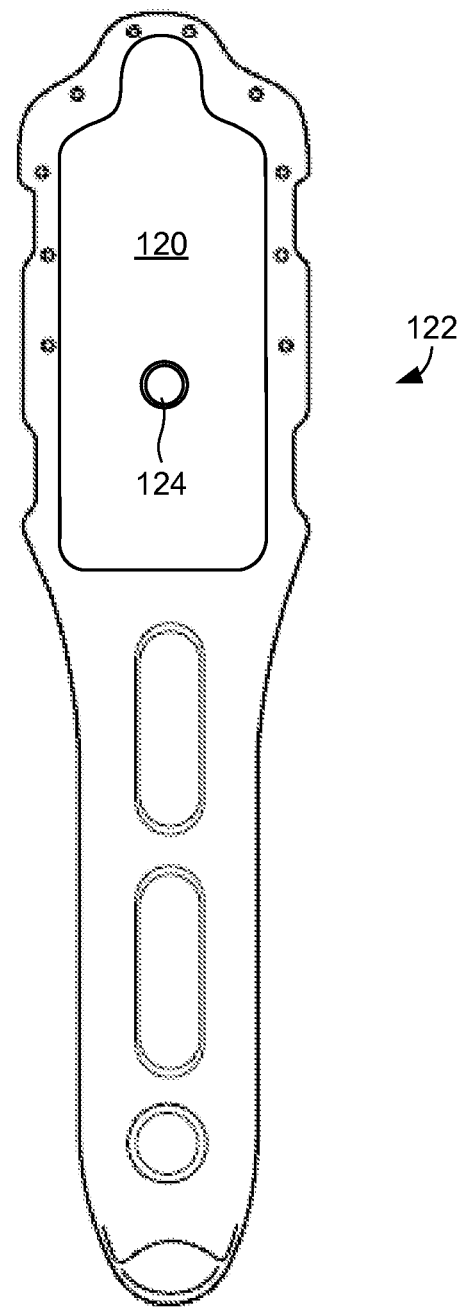
FIG. 10 is a top view of a humerus plate to which the locking plate of FIG. 9 has been applied.

After the humerus plate has been secured to the bone, a locking mechanism can be used to prevent the fasteners from backing out of the bone and the plate. FIG. 9 illustrates an example locking plate 120 that can be used for this purpose. The plate 120 can comprise a plate of biocompatible material (e.g., stainless steel or titanium). As indicated in FIG. 10, the locking plate 120 can be sized and configured so as to cover the openings, and therefore fasteners, of the proximal portion of the humerus plate 122. In some embodiments, the locking plate 120 can be secured to the humerus plate 122 using a fastener (not shown) that passes through an opening 124 that aligns with the drill guide opening formed in the humerus plate.

Testing was performed to evaluate the benefits of calcar fixation in restoring medial stability. Eleven matched pairs of fresh-frozen cadaveric humeri were obtained from donors with a mean age of 69.5 years (range, fifty-four to eighty-one years) at the time of death and were stripped of all soft tissues. Dual energy x-ray absorptiometry (DXA) scans of each humerus were performed to provide a measure of bone mineral density within the humeral head. Prior to testing, each specimen was analyzed with fluoroscopy to ensure that there were no preexisting osseous defects. The proximal part of each humerus was osteotomized to create a standard three-part fracture involving the surgical neck and greater tuberosity. Five matched pairs were randomly assigned to have the medial calcar region remain intact and were designated as the non-comminuted group. The other six matched pairs had removal of a 10 mm medially based wedge of bone to simulate medial comminution or a fracture that lacks a medial buttress. These specimens were designated as the medial comminution group. Fracture fixation with use of a commonly used proximal humeral locking plate was performed by an orthopaedic surgeon according to the surgical technique guide. In order to optimize fixation, all of the fixation constructs had seven proximal locking screws placed in the subchondral bone. Within each pair of humeri, one shoulder was randomized to have calcar fixation (with use of two screws crossing the fracture into the humeral head) while the other did not have calcar fixation (with use of two short screws that did not cross the fracture). These were designated as the fixation and no-fixation specimens, respectively.

Mechanical testing was performed with use of a previously established method in which the distal humeral condyles were removed and the humeral shaft was potted in polymethylmethacrylate COE Tray Plastic (GC America, Chicago, Ill.) within an aluminum cylinder. This construct was then fixed in steel tubing that was welded to a base plate at 20° from vertical. Vertical compressive loads were applied to the superior aspect of the humeral head, 0.5 cm medial from the bicipital groove, with use of a 2 cm diameter cupped cylinder, producing axial and shear loading of the fixation. The constructs were loaded to failure at a rate of 10 cm/min with use of a uniaxial servo-hydraulic 858 Mini Bionix materials testing system (MTS Systems, Eden Prairie, Minn.). Actuator force and displacement were recorded with use of TestStar software (MTS Systems). Each trial was also recorded with a video camera to observe the onset and progression of the different modes of failure and to establish the point of failure on load-displacement curves.

The specimens with medial comminution were observed to angulate immediately upon application of the load with slippage along the medial fracture line, which was accompanied by pullout of the proximal screws. In these tests, the maximum load prior to closure of the medial cortical defect was considered as the load to failure. In contrast, the non-comminuted specimens were initially stiffer and resisted angulation on application of the load. As the loading increased, the medial fracture line expanded as a result of shearing and simultaneous angulation of the humeral head. In these tests, the load to failure was simply taken as the maximum load observed during the test.

After testing, the actuator load and displacement data were transferred to Excel software (Microsoft, Redmond, Wash.) to create load-displacement curves. Values of load to failure, energy to failure, and displacement at the time of failure were determined from the load-displacement curves obtained for each construct. In addition, stiffness (defined as the slope of the linear portion of the load-displacement curve) was also determined for each specimen.

The effects of fracture type (comminuted or non-comminuted) and calcar fixation (fixation or no fixation) on the outcomes of load to failure, energy to failure, stiffness, and displacement to failure, while accounting for bone mineral density, were determined. A multivariate, random intercept regression model was fitted for each outcome with use of SAS software (version 9.13; SAS Institute, Cary, N.C.). This technique properly accounts for the paired nature of the specimens and quantifies the degree of correlation between pairs. Estimated means were derived from regression equations. Various models were explored with bone mineral density being considered as a linear or categorical variable, and all interactions (fracture type by calcar stability, fracture type by bone mineral density, calcar stability by bone mineral density) were examined. The results were analyzed with a significance level of $p=0.05$.

The medial comminution group without calcar fixation had the lowest values of load to failure, energy to failure, and stiffness. Each of these values increased, in ascending order, for the medial comminution group with calcar fixation, the no-comminution group without calcar fixation, and the non-comminution with calcar fixation (see Table I).

TABLE 1

Biomechanical Properties of the Four Constructs Tested*

| Outcome | Calcar Fixation | | | P Value | |
| --- | --- | --- | --- | --- | --- |
| | No | Yes | Overall | Fracture Type | Calcar Fixation |
| Load to failure (N) | | | | 0.015 | 0.002 |
| Comminuted | 463 | 682 | 564 | | |
| Noncomminuted | 985 | 1205 | 1087 | | |
| Overall | 716 | 935 | | | |
| Energy to failure (Nmm) | | | | 0.13 | 0.006 |
| Comminuted | 1976 | 3255 | 2554 | | |
| Noncomminuted | 3985 | 5264 | 4563 | | |
| Overall | 2919 | 4198 | | | |
| Stiffness (N/mm) | | | | 0.25 | 0.14 |
| Comminuted | 117 | 140 | 127 | | |
| Noncomminuted | 146 | 170 | 157 | | |
| Overall | 131 | 154 | | | |
| Displacement at failure (mm) | | | | 0.77 | 0.20 |
| Comminuted | 6.9 | 7.6 | 7.2 | | |
| Noncomminuted | 7.3 | 7.9 | 7.6 | | |
| Overall | 7.1 | 7.7 | | | |

*The estimated means and p values from the regression model are adjusted for bone mineral density.

Both calcar fixation and medial comminution had a significant effect on the load to failure. As detailed in Table I, specimens with medial comminution had a significantly lower mean load to failure as compared with non-comminuted specimens ($p=0.015$). The average load to failure in comminuted specimens decreased by 48% (523 N) when compared with non-comminuted specimens. Also, the use of appropriate calcar fixation screws resulted in 31% higher average load to failure (219 N) than in specimens without calcar fixation. This difference was significant ($p=0.002$).

The average bone mineral density values for the comminuted and non-comminuted groups were 0.50 and 0.65, respectively. Bone mineral density was not a significant predictor of any outcome measure, regardless of fracture type or the presence of calcar fixation. However, bone mineral density improved the overall multivariate regression model fit and was included in each regression model as a linear term. The final models included terms for fracture type, calcar stability, and bone mineral density but did not include interaction terms as interactions were not significant. In the regression analyses, the interaction effects were small compared with the main effects. Therefore, interactions again were not included, resulting in equal slopes among the regressions. The effect of bone mineral density was linear. The final models contained terms for fracture type, calcar stability, and bone mineral density, all without any interactions.

Similarly, the mean energy-to-failure value for the comminuted specimens was 2009 Nmm (44%) lower than that for the non-comminuted specimens. However, this decrease in load was not significant ($p=0.13$). In contrast, the average energy to failure for the constructs employing calcar fixation was 1279 Nmm (44%) higher than the average value for the constructs without calcar fixation ($p=0.006$).

Stiffness was calculated as the slope of the linear portion of the load-displacement curve from the point of initial contact until marked discontinuity was observed, indicating failure. Although mean stiffness was 19% lower with comminuted specimens compared with non-comminuted specimens and 18% higher with calcar fixation than without, these differences were not statistically significant (p>0.1 for both). An increasing trend in average stiffness was observed among the different test groups (Table I), with the comminuted specimens (without calcar fixation) having the lowest value and the non-comminuted specimens (with calcar fixation) having the highest. Similarly, regression analysis showed that neither medial comminution nor calcar fixation had a significant effect on displacement at the time of failure (p=0.77 and p=0.20 respectively). Mean displacement 5% lower with comminuted specimens compared with non-comminuted specimens and 8% higher with calcar fixation than without. However, these differences were not significant (p>0.2 for both).

In view of these test results, it can be appreciated that calcar fixation significantly improves the stability of repaired fractures and is recommended as a surgical option, regardless of the achievement of an anatomic reduction with cortical contact medially. The results demonstrate the biomechanical advantage of medial cortical contact and calcar fixation and they provide an explanation for the results that are seen clinically.

The invention claimed is:

1. A proximal humerus fracture fixation system comprising:
   an implantable humerus plate comprising:
      a proximal portion adapted to be positioned at a head and medial calcar of the humerus, and
      a distal portion adapted to be positioned along a shaft of the humerus,
      the proximal portion defining a plurality of calcar openings through the proximal portion, the calcar openings adapted to receive calcar fasteners that extend into the medial calcar; and
   an aiming apparatus comprising:
      a body that attaches to the proximal portion of the humerus plate,
      an elongated arm that extends laterally from the body and that curves to extend in a direction that is perpendicular to a plane in which the body is located, the elongated arm defining an elongated slot curved along a length of the elongated arm and
      a guide member that is mounted to the arm, wherein the guide member is adapted to guide pins or fasteners into the humeral head, and the guide member being movable along a length of the elongated slot.

2. The system of claim 1, wherein the guide member is adapted to guide pins or fasteners into the humeral head in an anterior-to-posterior direction.

3. The system of claim 1, further comprising a compression device adapted to press bone fragments together before final fixation of the humerus plate.

4. The system of claim 1, wherein the distal portion has a first slot having a length of approximately 12 to 20 mm and a width of approximately 3 to 6 mm.

5. The system of claim 1, further comprising a locking plate configured to abut the proximal portion and cover the plurality of calcar fasteners and to cover a plurality of proximal fastener openings in the proximal portion.

6. The system of claim 1, further comprising a plurality of calcar fasteners sized to extend through the calcar openings and into the medial calcar, wherein the calcar fasteners for the distal calcar openings are shorter than the calcar fasteners for extending through the proximal calcar openings, wherein the guide member is adapted to guide pins or fasteners into the humeral head in a direction that is perpendicular to the plurality of calcar fasteners.

7. The system of claim 1, wherein, the proximal portion of the humerus plate includes lateral sides having notches adapted to receive tabs of the aiming apparatus configured to attach to the humerus plate with a snap-fit.

* * * * *